US012213794B1

(12) United States Patent
 Schnitta

(10) Patent No.: US 12,213,794 B1
(45) Date of Patent: Feb. 4, 2025

(54) HEALTH CONDITION DETECTION AND REPAIR SIGNAL PROCESSING SYSTEM

(71) Applicant: Bonnie S. Schnitta, East Hampton, NY (US)

(72) Inventor: Bonnie S. Schnitta, East Hampton, NY (US)

( * ) Notice: Subject to any disclaimer, the term of this patent is extended or adjusted under 35 U.S.C. 154(b) by 724 days.

(21) Appl. No.: 16/803,704

(22) Filed: Feb. 27, 2020

Related U.S. Application Data

(60) Provisional application No. 62/811,458, filed on Feb. 27, 2019.

(51) Int. Cl.
 *A61B 5/38* (2021.01)
 *A61B 5/00* (2006.01)
 *A61B 5/30* (2021.01)
 *A61B 5/374* (2021.01)
 *A61B 5/375* (2021.01)

(52) U.S. Cl.
 CPC ............. *A61B 5/38* (2021.01); *A61B 5/0006* (2013.01); *A61B 5/30* (2021.01); *A61B 5/374* (2021.01); *A61B 5/375* (2021.01); *A61B 5/4064* (2013.01); *A61B 5/72* (2013.01)

(58) Field of Classification Search
 None
 See application file for complete search history.

(56) References Cited

U.S. PATENT DOCUMENTS

| 2006/0079773 A1* | 4/2006 | Mourad | A61B 5/031 600/438 |
| 2009/0163828 A1* | 6/2009 | Turner | A61B 5/38 600/559 |
| 2011/0295166 A1* | 12/2011 | Dalton | A61B 5/125 601/47 |
| 2016/0008568 A1* | 1/2016 | Attia | A61B 5/486 600/28 |

FOREIGN PATENT DOCUMENTS

WO   WO-2019010540 A1 *  1/2019   .......... A61B 5/0075

OTHER PUBLICATIONS

M. Ahmadvand, The Empirical Assessment of Human Vibration Propagated in Building and HVAC Systems, Inter.noise 2014 (Year: 2014).*

(Continued)

*Primary Examiner* — Devin B Henson
*Assistant Examiner* — Matthew Eric Ogles
(74) *Attorney, Agent, or Firm* — John F. Vodopia

(57) ABSTRACT

A method for identifying a subject's response to a sound signal includes using a capture device to capture a baseline bioelectric or vital sign response signal from a portion of a subject's body in an unexcited state for a first time period, directing a first predetermined sound, or a set of predetermined sounds, at the portion of the subject's body for a second time period, using the capture device to capture a responsive bioelectric or vital sign response signal from the portion of the subject's body during the second time period and processing the responsive bioelectric or vital sign (Continued)

response signal to determine a state of the portion of the subject's body or a responsiveness of the subject's body to the predetermined sound, or the set of predetermined sounds directed thereto during the second time period.

20 Claims, 6 Drawing Sheets

(56) References Cited

OTHER PUBLICATIONS

T. Nilsson, Vibration Exposure and Myocardial Infarction Incidence: the Vheep Case-Control Study, Occupational Medicine, vol. 56, pp. 338-344, 2006 (Year: 2006).*
T. Matoba, Evaluation of Frequency Weighting (ISO 2631-1) for Acute Effects of Whole Body Vibration on Gastric Motility, Journal of Sound and Vibration 253(1), pp. 31-36, 2002 (Year: 2002).*
S. Benton, A Review of Published Research on Low Frequency Noise and Its Effects, Department for Environment, Food and Rural Affairs, 89 pages, 2003 (Year: 2003).*
B. Schnitta, Acoustic Phenomena Found in People With Cancer and Thyroid Problems, The Journal of the Acoustical Society of America, 137, 2320, Abstract only, 2015 (Year: 2015).*

* cited by examiner

HEALTH CONDITION DETECTION AND REPAIR SIGNAL PROCESSING SYSTEM

CROSS-REFERENCE TO RELATED APPLICATIONS

This application derives the benefit of the filing date of U.S. Provisional Patent Application No. 62/811,458, filed Feb. 27, 2019, the content of which provisional application is incorporated herein by reference.

BACKGROUND OF INVENTION

The present invention relates broadly to a subject's response to sounds, and more particularly relates to identifying a subject's bioelectric response, or vital sign(s) response to one or more predetermined sounds to which the subject is exposed, and generating a health-related determination for the subject based on the response.

It is recently well documented and researched that vibration exposure has a correlation to cardiac and gastric disorders. Farhad Forouharmajd, Masoumeh Ahmadvad, THE EMPIRICAL ASSESSMENT OF HUMAN VIBRATION PROPAGATED IN BUILDING AND HVAC SYSTEMS, InterNoise (November) 2014; Ishitake, T., Noguchi R., Ando H., Matoba T.; EVALUATION OF FREQUENCY WEIGHTING (ISO 2631-1) FOR ACUTE EFFECTS OF WHOLE-BODY VIBRATION ON GASTRIC MOTILITY, J. Sound Vibration. 2002, 253 (1): 31-6; Bodil Bjor, LB, Tohr Nilsson and Christina Reuter, WALL VIBRATION EXPOSURE AND MYOCARDIAL INFARCTION INCIDENCE, 2006; Council NR, Panel on Musculoskeletal Disorders, The Workplace Institute of Medicine, Musculoskeletal disorders and the workplace: low back and upper extremities, 2001.

Exposure of the human body to high intensity vibrations for a long time, when exposure time is out of the defined permissible threshold, likely will cause physical and physiological disorders. Ebrahimi, H., INVESTIGATION OF NOISE AND VIBRATION EXPOSURE OF TEHRAN'S BUS DRIVERS, Tehran University of Medical Sciences. High intensity vibrations are extreme and are easily felt and measured. ASHRAE, the American society of heating, refrigerating and air-conditioning engineers organized to advance the arts and science of heating, ventilation, air conditioning and refrigeration clearly outlines acceptable limits to exposure to high intensity vibrations. Farhad Forouharmajd, Masoumeh Ahmadvad, THE EMPIRICAL ASSESSMENT OF HUMAN VIBRATION PROPAGATED IN BUILDING AND HVAC SYSTEMS, InterNoise (November) 2014.

Likewise, a growing group of people are known to experience an increased sensitivity to low frequency sound. Such people complain about the presence of hum, buzz, and rumble that are often not recognized as a nuisance or disturbance, since the majority of people do not perceive or are disturbed by these very low frequencies, yet these low frequency noises may have serious health effects like vertigo, disturbed sleep, stress, hypertension, and heart rhythm disorders; M. Oud, LOW FREQUENCY NOISE: A BIOPHYSICAL PHENOMENON, Congress Geluid, Trillingen, Luchtkwaliteit en Gebied & Gebouw, 2012; G. Leventhall, P. Pelmear and S. Benton, A REVIEW OF PUBLISHED RESEARCH ON LOW FREQUENCY NOISE AND ITS EFFECTS, Report for Dept. for environment, food and rural affairs, London (2003).

Additional research has shown that there is a further correlation of the inverse evidence that people of ill-health or with a health condition have an extreme sensitivity to various sounds or a specific frequency or decibel level; B. Schnitta (2015). ACOUSTIC PHENOMENA FOUND IN PEOPLE WITH CANCER AND THYROID PROBLEMS, 169th Meeting of the ASA, Pittsburgh, PA. Typically, a singular tone or vibration to which such people of ill-health, people who are at the beginning stages of a health condition even before it has been diagnosed, or people with a known health condition are extremely sensitive is low frequency. This noise sensitivity is often true where someone is born with a predisposition to a medical condition, such as hearing sounds that others do not hear when they are young and then coming down with cancer years later. But while it is more common that the disturbing reaction to a hum, buzz and/or rumble sound occurs when the hum, buzz and/or rumble sound is low frequency, this is not always the only acoustic scenario.

Also, there are other people with a medical condition that are disturbed by only a transient of any frequency, such as a high frequency sweep, loud short burst of sound, etc. Although it is not a singular acoustic event, it is consistent that those of ill health or with a medical condition hear sounds or tones that others often cannot hear or are disturbed and are disturbed by same sensitivity, i.e., "reception;" (B. Schnitta (2015). ACOUSTIC PHENOMENA FOUND IN PEOPLE WITH CANCER AND THYROID PROBLEMS, 169th Meeting of the ASA, Pittsburgh, PA), just as there are those that are easily calmed by tone of a certain frequency, song, or certain sounds or music.

Electroencephalography (EEG) records the neural activity of electrical potential across cell membranes, which are detected through the cerebral cortex and recorded by a plurality of electrodes. EEG data tells us that the changes in electrical potential in the cerebral cortex contain rhythmical activity, which typically occurs at frequencies of about 0.5 to 70 cycles per second (hertz). While asleep, more predictable signals are generated at a low voltage and at predictable frequencies that occur over predictable periods.

SUMMARY OF THE INVENTION

The present invention overcomes the shortcomings of the prior art.

Five distinct brain wave patterns that are commonly detected during an EEG recording are delta waves (0.5-3 Hz), theta waves (3-8 Hz), alpha waves (8-12 Hz), beta waves (13-38 Hz), and gamma waves (38-100 Hz). Although these frequency ranges can vary from person to person they set the foundation for part of this invention. As electronic monitoring of brain wave frequencies evolves, the refinement of our understanding of brain wave frequencies and activities improves. Such improved understanding of brain wave frequencies and activities provides a foundation for at least a portion of the proposed invention.

The invention takes the value in detected brain activity to another level noting the additional correlation between the detected brain activity and easily obtained vital signs, such as blood pressure, pulse, oxygen levels, etc. and a state of mental and/or physical health. In addition to a basis from an understanding of brain wave frequencies and activities, an understanding of transcranial magnetic stimulation (TMS) also provides a foundation for at least a portion of the proposed invention. As is known, TMS refers to a noninvasive excitation of neurons in the brain by utilizing magnetic fields to induce electric currents in the brain. An example of a TMS application includes placing a treatment coil that generates a magnetic field near a subject's head, where the generated magnetic field induces an electrical current in the brain causing neurons to fire, which may induce various chemical reactions.

Methods, systems and apparatuses are described herein for active brain stimulation that leverage available knowledge, for example, to enhance memory consolidation by stimulating neurophysiological events. When the person tries to control the brain to achieve a certain frequency state, such as an alpha state, this is often referred to as biofeedback (see www.psychologytoday.com/blog/the-athletes-way/201504/alpha-brain-waves-boost-creativity-and-reduce-depression). Additionally, there is certain music that helps us think (see www.brainleadersandlearners.com/multiple-intelligences/musical/the-brain-on-music), and/or heal (see www.brainwavetraining.com/brainwave.htm).

In an embodiment, the inventive method and system captures and processes signals representative of magnetically induced currents of the brain, and/or magnetically or sonically induced currents in other portions of the body (referred to herein as "bioelectrical signals"), and/or other vital signs of the body, such as blood pressure, heart rate, pulse oximeter, or pulse, including but not limited to the bones, blood flow, oxygen levels and nerves of the body, that are associated with good health, or are an indication of poor health, physical injury, mental illness or disease, and processes same to realize a health-related determination. Please note that while the inventive method and system are described in relation to a person, or subject, the invention may be utilized to make a health-related determination for any animal.

In another embodiment, the invention provides a method for identifying a subject's response to a sound signal or signals. The method includes using a capture device to capture a baseline bioelectric signal, vital sign signal or both, captured from a portion of a subject's body in an unexcited state for a first time period, directing a first predetermined sound, of a set of predetermined sounds, at the portion of the subject's body for a second time period, using the capture device to capture a responsive bioelectric signal, vital sign or both, captured from the portion of the subject's body during the second time period, and processing the baseline or vital sign bioelectric signal and the responsive bioelectric signal, vital sign signal or both, to determine a state of the portion of the subject's body or a responsiveness of the subject's body to the predetermined sound signal that was directed thereto during the second time period.

The predetermined sound signal is a low frequency sound whether emanating from a speaker or other vibrating structure or membrane and wherein the directing includes directing the predetermined low frequency sound starting at an amplitude that by American society of heating, refrigerating and air-conditioning engineers ("ASHRAE") standards is defined as unperceivable and increasing the amplitude until a perceptible amplitude is reached. Alternatively, the predetermined sound signal is at a fixed frequency starting at an amplitude that by ASHRAE or other standards is defined as unperceivable and increasing the amplitude of the sound signal until an elevated amplitude is reached, or, the predetermined sound signal is a composite sound signal with portions defined by varying frequencies of fixed amplitude. Preferably, the predetermined sound signal is a composite sound signal with portions of the composite signal defined by varying frequencies or tones and increasing amplitude. For that matter, the amplitude increases in the portions of the composite signal as a function of the increasing frequencies.

Preferably, the fixed frequency is less than 1 Hz, but may be between 7 and 12.5 Hz, between 4 and 8 Hz, between 12 Hz and 40 Hz. Alternatively, the fixed frequency may be between 40 Hz and 100 Hz, 63 Hz or 125 Hz. Alternatively, the fixed frequency, tone or frequency range is a higher frequency, for example, greater than 125 Hz. Preferably, a frequency, tone, frequency range of the sound signal is varied over the second time period. For example, the frequency of the sound signal is varied from 0.1 Hz to 13 Hz and then 13 Hz and up over the second time period with each of these sweeps performed in increasing amplitude.

The method also may include a step of processing the determined state based on the baseline or vital sign bioelectric signal and the responsive bioelectric signal, vital sign signal or both, from the portion of the subject's body to render a medical diagnosis, and/or a step of processing the responsive bioelectric signal, vital sign signal or both to qualify and quantify the determined state based on the bioelectric or vital sign response signal from the subject's body to classify a suspected medical diagnosis of a medical condition related to the determined state. In that case, the step of processing further includes recommending one or more courses of action and preventive intervention for diagnosed medical condition. The inventive method may also include generating automatic communications, and sending the communications to a medical professional, such as in the form of an email or incorporated in an app or other method of communication that includes the analysis of the suspected medical condition. Preferably, the method includes directing a predetermined sound signal, whether in the audible range or not, at or on the portion of the subject's body to facilitate treatment or expedite healing of the suspected medical condition.

In another embodiment, the invention provides a system for identifying a subject's response to sound signal(s). The system includes a capture device for capturing a baseline bioelectric signal, vital sign signal or both, from a portion of the subject's body in an unexcited state, during a first time period, a sound generating device for generating and directing a first predetermined sound signal, from a set of predetermined sounds, at the portion of a subject's body for a second time period. The capture device captures a responsive bioelectric response signal from the subject during the second time period typically beginning immediately at an end of the first time period. A processor with memory processes the baseline bioelectric or vital sign signals, and the responsive bioelectric response or vital sign signal or both, to determine a state of the subject or a responsiveness of the portion of the subject's body to the first predetermined sound signal directed thereto.

Preferably, the first predetermined sound is generated in a frequency range between 1 and 40 Hz. The first predetermined sound may be swept through a frequency range beginning at a low frequency of 40 Hz and increasing to a high frequency at 10,000 Hz. In that case, the low frequency may be as low as is 1 Hz and the high frequency may be as high as 20,000 Hz. Alternatively, the first predetermined sound signal is swept through range from the low to high frequency and then swept in an increasing amplitude from roughly 20 dB below baseline to high amplitude known not to cause hearing loss for the short time, such as 80 dB (A) (A weighted), depending on the length of the sound signal. Each of the set of predetermined sound signals corresponds to a respective probability that it is associated with a portion of the subject's body and health condition.

Alternatively, each of the set of predetermined sound signals corresponds to a respective probability that it is associated with a portion of the subject's body and health condition and then stored and classified for an improved pattern recognition in the future, whether that is for the patient or general population for a specific state of health. Preferably, the subject's body is quantified as a number N of body portions, where N is an integer number, wherein N respective baseline signals are captured for each of the N body portions, wherein each of the body portions are subjected to the first predetermined sound signal and wherein a number N of respective signal responses are captured from each of the N portions, respectively. Then, each of the N body portions are subjected M predetermined sounds varying in frequencies and/or amplitude, where M is an integer, and wherein M signal responses are captured for each of the N body portions.

In another embodiment, the invention provides a system for identifying a subject's response to low frequency sound signals. The system includes a capture device for capturing one or more baseline bioelectric signals or vital sign signals from a portion of the subject's body in an unexcited state, and a sound/vibration generating device for generating and directing a first predetermined sound, of a plurality of predetermined sounds, at the portion of the subject's body for a second time period. The capture device captures a bioelectric response signal, vital signs or both from the portion of the subject's body during the second time period typically beginning immediately at an end of the first time period. A processor with memory processes the baseline bioelectric signal, vital sign signal or both, and the responsive bioelectric or vital sign signals to determine a state of the portion of the subject's body or a responsiveness of the portion of the subject's body to the first predetermined sound directed thereto. Preferably, a baseline bioelectric or vital sign signal, and a bioelectric or vital sign signal responsive to the first predetermined sound signal are captured for each portion of the subject's body. Each portion of the subject's body, a respective second through N predetermined sound signal, where N is an integer, of the predetermined sound signals is directed to the each portion, and bioelectric signal responses are captured therefrom.

BRIEF DESCRIPTION OF THE DRAWINGS

Further features and advantages of the invention will become apparent from the description of embodiments that follows, with reference to the attached figures, wherein.

DETAILED DESCRIPTION OF THE INVENTION

The following is a detailed description of example embodiments of the invention depicted in the accompanying drawings. The example embodiments are presented in such detail as to clearly communicate the invention and are designed to make such embodiments obvious to a person of ordinary skill in the art.

FIGS. 1-4 present examples of bioelectrical signals and/or vital sign signals. The signals may be captured when a subject is in a non-excited state, or during a subject's exposure to certain sound signals, for example, where the subject is in a disease state, a pre-disease state or a non-disease state. This is because some of the examples are straight forward like a person with a thyroid condition being sensitive and disturbed by the sound of a helicopter, or a cancer patient even before the diagnosis of cancer being sensitive and disturbed by a structure borne sound, such as from a condenser unit not installed on proper vibration isolators. On the other hand, the sensitivity can be patient specific.

Figure 1:
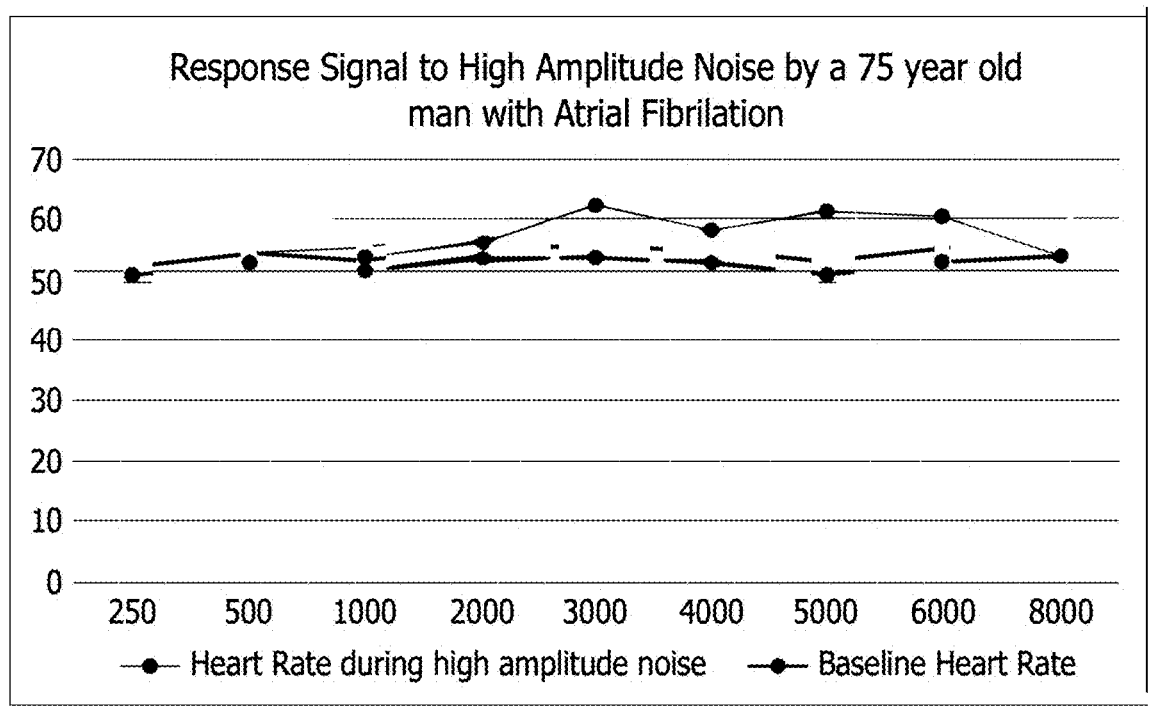
FIG. 1 presents a comparison of a baseline heart rate signal of a 75 year old man with atrial fibrillation issues with a heart rate signal of the same man captured while the man is subjected to a sound signal that varies in frequency but is triggered when the frequency and amplitude become high.

In greater detail, FIG. 1 depicts heart rate signals derived from a patient with atrial fibrillation (afib) who all of a sudden reported as being is disturbed by the sound of several children. The sensitivity to high frequency and high amplitude sounds indicates a diagnosis of afib that would show up when the vital sign or bioelectric reaction was compared to a baseline (see arrow at beginning of irregular heartbeat)

The invention captures (and relies upon) signals representative of natural currents of the brain, and other portions of the body (referred to interchangeably with "bioelectrical signals"), and/or other vital signs of the body, such as blood pressure, heart rate, pulse oximeter, or pulse including but not limited to the bones, blood flow, oxygen levels and nerves of the body, that are associated with good health, or are an indication of poor health, physical injury, mental illness or disease. The invention then subjects portions of the subject's body to excitation sound signals, and captures responsive biometric or vital sign signals for comparison to the baseline signals. Examples of one or more of these signals are shown in FIG. 1-4. But while these figures only show 4 examples, they are presented for exemplary purposes only and not meant to limit the scope and spirit of the invention; bioelectrical signals and vital signs are extensive. This is because some bioelectrical signals relied upon by the invention are straight forward, like a person with a thyroid condition being sensitive and disturbed by the sound of a helicopter, or a cancer patient even before the diagnosis of cancer being sensitive and disturbed by a structure borne sound, such as from a condenser unit not installed on proper vibration isolators. On the other hand, the sensitivity can be patient specific.

In a first testing configuration, preferably after a baseline signal is captured, or a normalized baseline signal is available, a subject, while wearing a cap, band, or any device that is attached to the head or body that can detect bioelectric current signals, or vital sign signals (hereinafter, the "capture device"), listens to (is subjected to) sounds, including some forms of speech or slurred speech from a speaker or other vibrating structure played at various vibratory states, frequencies and levels of amplitude, for example, in a known or controlled acoustic environment. This sound, whether a tone, sweep of tones or other variation of frequencies, or variations in speech all at different amplitudes (hereinafter, the "sound signal"), induces a response in the brain of certain subjects undergoing the sound signal exposure. The response is captured as a responsive or reactive bioelectric signal by the capture device The frequency/amplitude responsive or reactive bioelectric response signal is monitored, i.e., is captured by the capture device attached to the subject's body, for example, the head. Even a capture device as small as a pad that a hand or finger is placed on or a wearable device on the ear, wrist, or finger can collect bioelectric data responsive to the sound signal and/or baseline bioelectric or vital sign signals when the subject is not exposed to the sound. This first configuration is intended to capture the subject's bioreaction to the sound to which he/she is exposed, even though other configurations can capture a bioelectric signal reaction from a body portion other than the subject's brain, such as a possible broken bone, kidney infection, or missing cartilage. The bioelectric signals captures by the capture device are then processed.

The processing of the subject's response to the sound signal to which he/she is exposed, that is captured by the capture devices ("response signal") is understood, when compared to the baseline or vital sign signal representative to the subject's passive state, provides a reasonable indication of the overall physical, psychological, or chemical condition of the subject. The inventive system compares the instantly captured responsive bioelectric signal(s), compares same to the baseline signal(s) (both bioelectric signals), captured at the earlier time, and assessed to identify differences therebetween, and based thereon, assessment of the subject's state.

Figure 2:
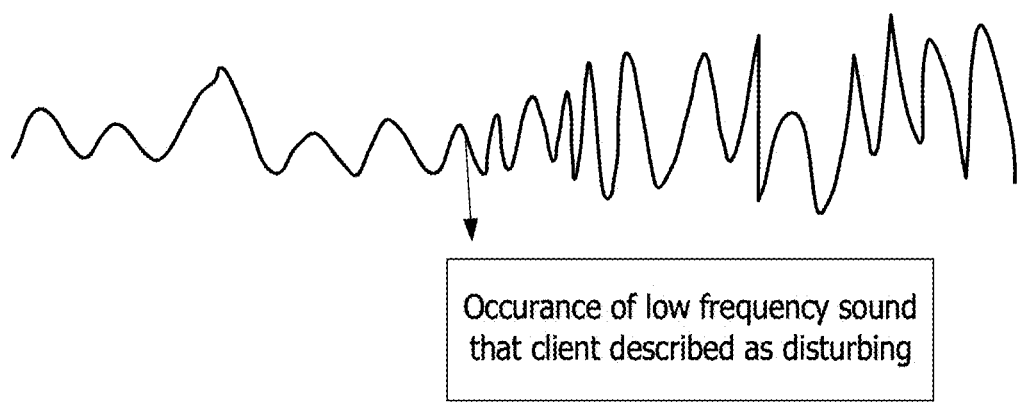
FIG. 2 presents a graph of brain waves captured when a sound signal indicates a disease, such as a precancerous tumor.
Figure 3:
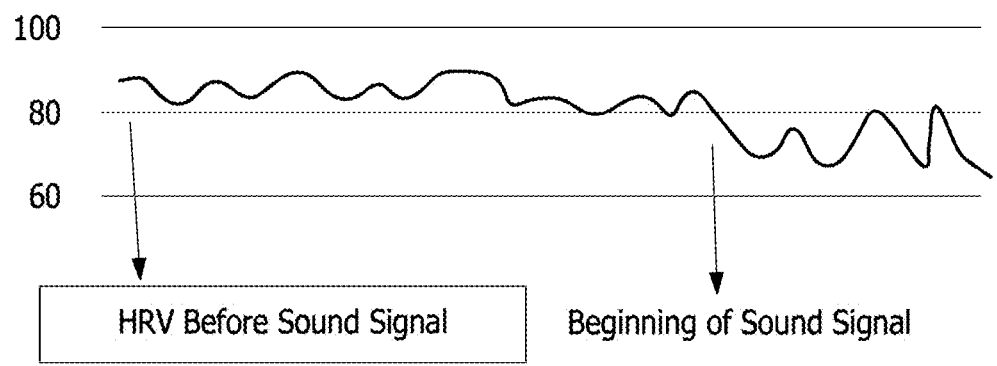
FIG. 3 presents a graph of heart rate of a subject before (left of arrow "beginning of sound signal") the subject is subjected to a sound signal and after (right of arrow)
Figure 4:
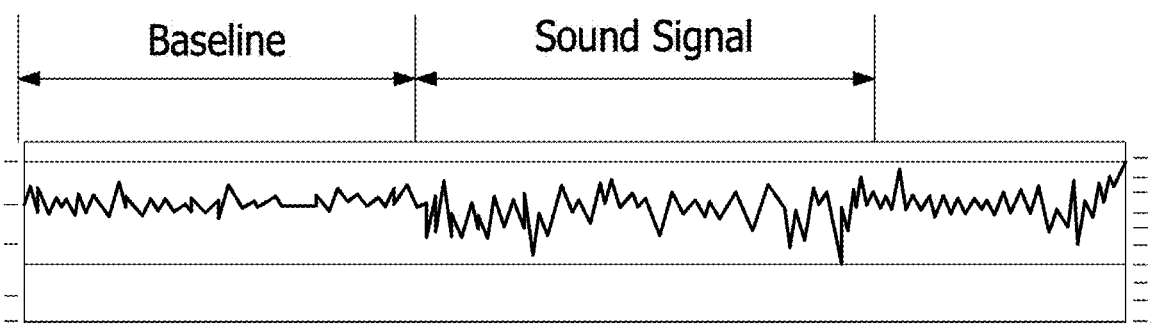
FIG. 4 presents a graph of a pulse oxemitry reading (signal) for a subject both before ("Baseline") and after a sound signal is directed to the subject.

As an example, for FIG. 1, a baseline maximum of 55 is registered for a 75-year-old man. Frequencies of low to high frequency repeated for increasing amplitude are played and the signal remains the same. After the sound signals associated with atrial fibrillation (high frequency and loud) are played to the patient it is captured that it becomes greater than 55 and exceeds 60. FIG. 2 shows the beginning of a test where a person is having their brain wave activity monitored. The regularity of the frequency and amplitude is noted. This can be visually noted at the time of the test or sent to a file to be reviewed visually later or could go into a signal processing system. A low frequency sound signal, known to disturb people with thyroid and cancer, is played. At that moment it is played the frequency and amplitude change significantly. Again, this can be visually noted at the time of the test or sent to a file to be reviewed visually later or could go into a signal processing system. One method that this signal processing system can note the event is to have the signal processed with a standard adaptive AR (autoregressive) or ARMA (autoregressive moving average). At the time of the event (reaction to the disturbance) a significant error function is generated, and the event is flagged.

The subject's instantly captured bioelectric response signal(s) enables the health care practitioner to identify a health condition even when a subject does not have the ability to verbalize the health condition, such as in the case of the subject being a human in a coma a human that is mute or an animal, not wanting to admit to a health condition, or not knowing how to define a condition, when tests results provide a false negative, etc. As stated, the capture device is wrapped around or placed under an arm, wrist or leg (rather than the subject's head), and the instant response is captured. Then, the instantly captured signals is processed with the baseline (or passive) captured response to identify differences in the subject's state that will indicate some irregularity in the human condition, such as thyroid problems, atrial fibrillation, cancer, post-traumatic stress disorder, missing cartilage, a broken bone or nerve damage. If there is no prior recorded response or baseline for comparison, the invention compares the instant captured response to a standardized response signal, as is explained in greater detail below herein.

There are various capture devices presently available to monitor bioelectrical signals and vital sign signals, as described above, with or without sound stimulation means. The inventive method, system and/or apparatus captures a baseline bioelectrical signal while the subject is in a passive state (not subjected to stimulating sound). When the sound system is activated, an excitation signal is generated and radiated/directed to the subject. The subject's response to the excitation sound signal is captured and processed, which may indicate a change in the EEG signal (brain wave), heart rate, or other vital sign (as shown by example in FIGS. 1-4). The excitation sound signal can be loud or barely audible or even inaudible of a particular frequency or frequencies. The bioelectric response or reaction signal is processed (assessed) to indicate a condition of good or poor health that is physical, psychological, or chemical.

For that matter, the inventive signal processing method, system and/or apparatus are configured to focus upon and recognize the pattern of the resultant responsive biometric response signal, generated in response to the stimulating (excitation) sound signal (or shock wave, for example), to identify a specific health condition, such as cancer or atrial fibrillation by the change in the subject's baseline. Each health condition causes a different reaction to certain frequencies loud sounds, or both. That is, in a diseased state, exposing the subject to loud sounds at varying frequencies is a disturbance to the person, and will be indicated by the change from the baseline to the responsive bioelectric signal. Thyroid and cancer is typically a low frequency and amplitude for a long duration, afib is typically a loud high frequency of short duration, back pain is typically a response to both, etc. Once the health condition has been identified, the capture device notes the health condition based on the signal response (to the excitation) and produces a report or visual display.

If applicable, the inventive system then generates a therapeutic sound that when directed to the specific area of interest of the subject's body for the determined health condition, at the correct frequency or frequencies, will promote healing or other tissue modification, such as growth of cartilage, a bone, a nerve, or other body tissue with or without the inclusion of the injection of stem cells.

The inventive signal processing method, system and/or apparatus relies upon a capture device for detecting brainwaves or other magnetic signals understood to reflect electrical currents flowing in parts of the body in conjunction or alternatively with vital signs, such as blood pressure, heart rate, diabetes, etc., as baseline bioelectric signals (without sound excitation), an apparatus for generating excitation sound signals at various frequencies or amplitudes in the existing acoustic environment or ambient, for example, at low frequencies and a signal processing device, for example, a microprocessor, app, or computer that can perform signal processing of the captured baseline brain or body signals, before exposure to excitation sound, and the responsive bioelectric signals, captured during exposure to the excitation sound (for example, low frequency sound signal), in order to compare the respective captured signals and accurately identify a physical, psychological, or chemical state of good or poor health of the subject under test/treatment.

Inventive Applications

In addition to the above, the inventive signal processing method, system and/or apparatus operates to identify sound(s) at a particular frequency or frequencies and/or particular associated amplitudes that are bothersome to a person, whether it is in a hospital, medical office, office, home, classroom or other location.

The invention correlates the disturbing sound at the particular frequency or frequencies and/or amplitude to correctly identify a physical, psychological, or chemical state of good or ill health, such as noting that when a transient high frequency and loud volume, like children screaming creates a change in bioelectric response, vital signs or both, then the system triggers a response that there is a possible diagnosis of afib and the person is referred to a doctor for further evaluation. It can also identify pain, or the body's chemical response to pain management, in a person independent of a reported pain, or show a little evidence of pain even when the individual reports severe pain. That is, noting FIG. 2, someone can report to be in a great deal of pain. A person in a great deal of pain will typically have a change in frequency that if often erratic when certain sounds are made. Often these sounds are associated with what caused the pain, such as a loud noise much like an explosion or thump such as from a serious fall. Someone who reports pain, but does not have any pain will, after the brain wave has settled to a baseline, there will be no pattern change as frequencies and amplitude increases for the frequencies are played.

The inventive signal processing method, system and/or apparatus correlates the disturbing sound at the particular frequency or frequencies and/or amplitude to correctly identify a physical, psychological, or chemical state of poor health, such as early stages of breast or thyroid cancer, or atrial fibrillation even prior to the first symptoms or diagnosis.

Figure 5A:
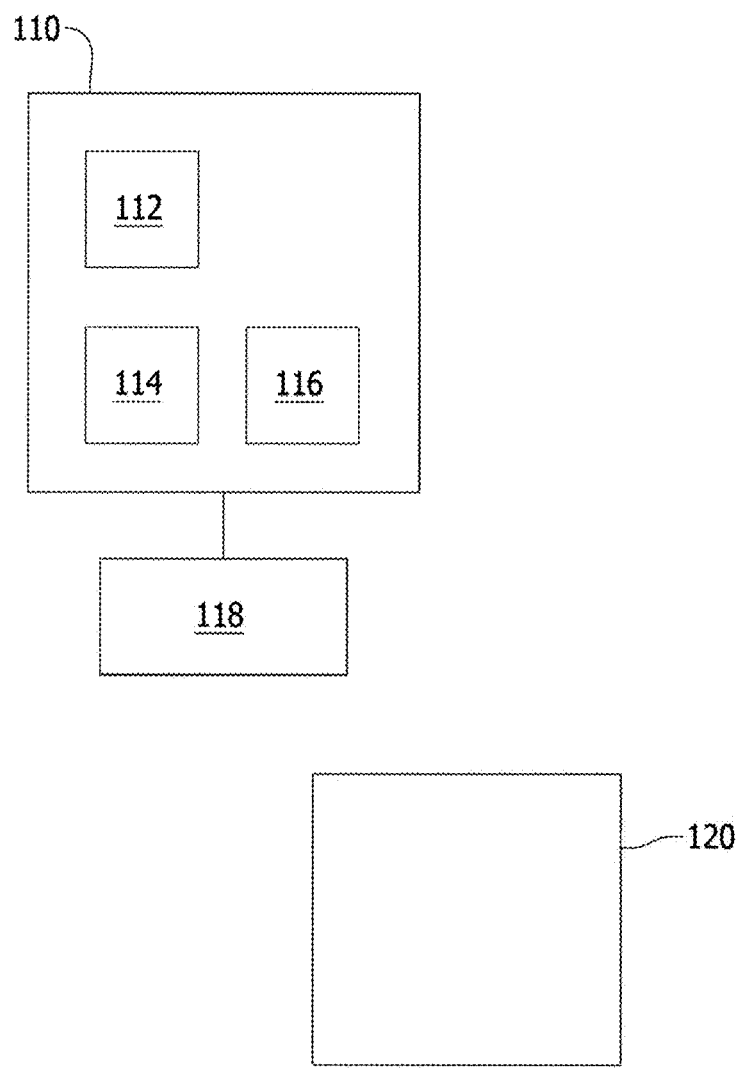
FIG. 5A depicts one embodiment of an inventive system programmed to implement the invention.

FIG. 5A depicts one embodiment of the invention that includes a computer 110, and a sound transmitting and receiving device 120. The computer 110 includes inter alia a processor 112, a memory 114, and an I/O device 116 and input device 118, any portion of which can be on a cloud. The computer may be a server, a laptop, a desktop, a smartphone, an iPad or other tablet, etc., without limitation. Computer readable instructions are downloaded to the computer or app on a phone, and stored in memory, such as memory 114. When the processor 112 operates on the computer readable instructions, the application program controls operation of the sound transmitting and receiving device 120.

Preferably, a baseline bioelectric signal is captured using one or more bioelectric signal capture devices, where the subject is in a passive state, i.e. has not been exposed to an excitation sound signal from a sound transmitting and receiving device 120. The sound transmitting and receiving device 120 generates a sound excitation signal and radiates the sound excitation signal at the subject. The bioelectric signal capture devices capture one or more responsive bioelectric response signals in response to the excitation. Alternatively, part of the excitation signal that is reflected from the subject, may be captured by the device 120 (in a receiver mode rather than a transmit mode), for processing as a bioelectric response signal. The sound transmitting and receiving device 120 provides the captured signal(s), which are bioelectric signals, vital sign signal or both, to the processor 112.

Figure 5B:
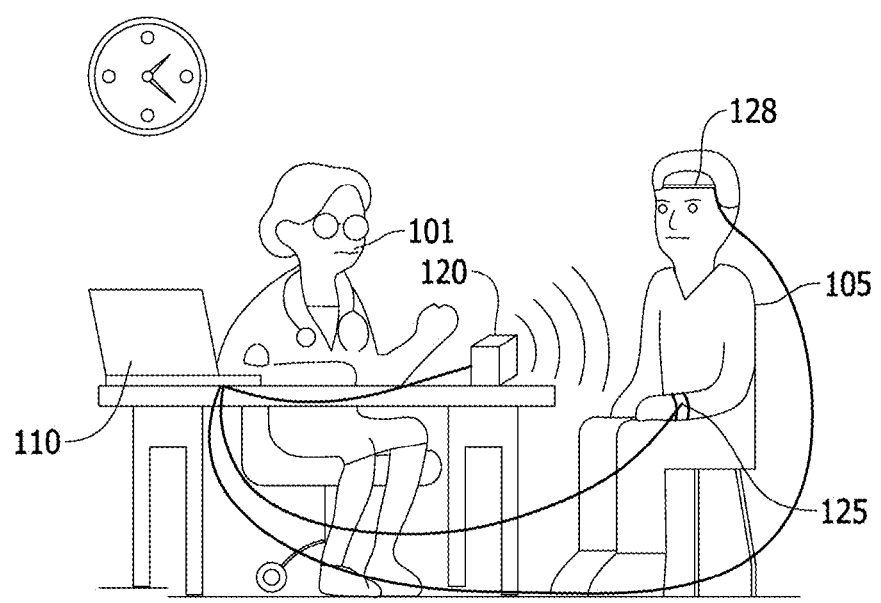
FIG. 5B depicts an example of the inventive system being used to examine a subject.

The processor 112 processes the captured baseline (as the case may be) and responsive bioelectric response signals. If there is an available baseline signal for that portion of the subject's body from which the instant bioelectric response signal is derived, the bioelectric response signal is compared to the baseline signal. If not, the captured response signal is compared against a standard, or generalized baseline signal. FIG. 5B depicts a professional 101 testing a subject 105 using the computer 110, and operational application program therein, in cooperation with sound transmitting device 120 and a first bioelectric signal capture device 125, for capturing vital signs like heart rate, blood oxygen level, pulsatility, etc. and a second bioelectric signal capture device 128, for capturing vital signs like brain wave activity, pressures, etc., without limitation. Please note, however, that the drawing is for exemplary purposes only and is not meant to limit the invention to these bioelectric signal capture devices. For example, in an alternate application, a subject may "wear" headphones and the wires, or Bluetooth signals from the capture devices, provide the responsive bioelectric signals, vital sign signals or both to the processor 112.

Please note that the computer may operate as a remote server to the sound transmitting and receiving device 120, where they are connected though a LAN, virtual LAN or the Internet.

As will be evident to persons skilled in the art, the foregoing detailed description, applications and figures are presented as examples of the invention, and that variations are contemplated that do not depart from the fair scope of the teachings and descriptions set forth in this disclosure.

What is claimed is:

1. A system for identifying a subject's response to sound signal, comprising:
   means for capturing a baseline signal from a portion of the subject's body in an unexcited state for a first time period when there are no predetermined sounds being directed to the subject's body, and means for storing said baseline signal, where said baseline signal is a bioelectric or vital sign signal;
   means for directing a first predetermined sound, of a set of predetermined sounds, at the portion of the subject's body for a second time period;
   means for capturing a responsive signal from the portion of the subject's body during the second time period, and means for storing said responsive signal, where said responsive signal is said bioelectric or vital sign signal;
   means for comparing said baseline signal and said responsive signal to determine any differences therebetween, said any differences relied upon to determine a state of the portion of the subject's body, said determined state excited by the first predetermined sound signal directed thereto during the second time period;
   means for processing said determined state based on said baseline signal and said response signal from the portion of the subject's body to render a medical diagnosis; and
   means for recommending one or more courses of action and preventive intervention for the medical diagnosis;
   wherein:
   the baseline and responsive bioelectric and vital sign signals include heart rate signals;
   the first predetermined sound is a high frequency, high amplitude sound;
   the differences determined between said baseline signal and said responsive signal includes a differential to the heart rate; and
   the medical diagnosis is atrial fibrillation.

2. The system according to claim 1, wherein the first predetermined sound signal is a low frequency sound whether emanating from a speaker or other vibrating structure or membrane and wherein said means for directing includes means for directing the predetermined low frequency sound starting at an amplitude defined as unperceivable by American society of heating, refrigerating and air-conditioning engineers ("ASHRAE") standards and increasing the amplitude until a perceptible amplitude is reached.

3. The system according to claim 1, wherein said means for directing includes means for directing the first predetermined sound signal at a fixed frequency starting at an amplitude defined as unperceivable by American society of heating, refrigerating and air-conditioning engineers ("ASHRAE") and increasing the amplitude of the sound signal until an elevated amplitude is reached.

4. The system according to claim 3, wherein said means for directing the first predetermined sound signal at a fixed frequency includes means for directing a fixed frequency greater than 125 Hz.

5. The system according to claim 3, wherein said means for directing the first predetermined sound signal at a fixed frequency includes means for directing a fixed frequency that is a high frequency greater than 1000 Hz.

6. The system according to claim 1, wherein said means for directing the first predetermined sound signal includes means for directing a composite sound signal with portions defined by varying frequencies of fixed amplitude.

7. The system according to claim 1, wherein said means for directing the first predetermined sound signal includes means for directing a composite sound signal with portions of the composite signal defined by varying frequencies, including increasing frequencies, and increasing amplitude.

8. The system of claim 7, wherein said means for directing the first predetermined sound signal includes means for increasing the amplitude in the portions of the composite signal as a function of the increasing frequencies.

9. The system according to claim 1, wherein said means for directing the first predetermined sound signal includes means for varying a frequency, tone, or frequency range of the sound signal over the second time period.

10. The system of claim 1 further including means for generating an automatic communication and sending said communication to a medical professional, in the form of an email, incorporated in an app or other method of communication that includes the medical diagnosis.

11. The system according to claim 1, wherein said means for recommending one or more courses of action includes means for directing a second predetermined sound signal, whether in the audible range or not, at or on the portion of the subject's body to facilitate treatment or expedite healing of the suspected medical condition.

12. The system of claim 1 wherein the first predetermined sound:
has a frequency of 10,000 Hz or less and
has an amplitude of 80 dB (A) (A weighted) or less.

13. A system for identifying a subject's response to sound signal, comprising:
means for capturing a baseline signal from a portion of the subject's body in an unexcited state for a first time period when there are no predetermined sounds being directed to the subject's body, and means for storing said baseline signal, where said baseline signal is a bioelectric or vital sign signal;
means for directing a first predetermined sound, of a set of predetermined sounds, at the portion of the subject's body for a second time period;
means for capturing a responsive signal from the portion of the subject's body during the second time period, and means for storing said responsive signal, where said responsive signal is said bioelectric or vital sign signal;
means for comparing said baseline signal and said responsive signal to determine any differences therebetween, said any differences relied upon to determine a state of the portion of the subject's body, said determined state excited by the first predetermined sound signal directed thereto during the second time period;
means for processing said determined state based on said baseline signal and said response signal from the portion of the subject's body to render a medical diagnosis; and
means for recommending one or more courses of action and preventive intervention for the medical diagnosis;
wherein:
the baseline and responsive signals are brain wave signals;
the first predetermined sound is a low frequency sound signal;
the differences determined between said baseline signal and said responsive signal is a differential in the brain wave activity; and
the medical diagnosis is precancerous or cancerous tumor.

14. The system of claim 13 wherein:
the first predetermined sound signal is a low frequency sound whether emanating from a speaker or other vibrating structure or membrane and wherein said means for directing includes means for directing the predetermined low frequency sound starting at an amplitude defined as unperceivable by American society of heating, refrigerating and air-conditioning engineers ("ASHRAE") standards and increasing the amplitude until a perceptible amplitude is reached.

15. The system of claim 13 wherein:
said means for directing includes means for directing the first predetermined sound signal at a fixed frequency starting at an amplitude defined as unperceivable by American society of heating, refrigerating and air-conditioning engineers ("ASHRAE") and increasing the amplitude of the sound signal until an elevated amplitude is reached.

16. The system according to claim 13, wherein:
said means for directing the first predetermined sound signal includes means for directing a composite sound signal with portions defined by varying frequencies of fixed amplitude.

17. A system for identifying a subject's response to sound signal, comprising:
means for capturing a baseline signal from a portion of the subject's body in an unexcited state for a first time period when there are no predetermined sounds being directed to the subject's body, and means for storing said baseline signal, where said baseline signal is a bioelectric or vital sign signal;
means for directing a first predetermined sound, of a set of predetermined sounds, at the portion of the subject's body for a second time period;
means for capturing a responsive signal from the portion of the subject's body during the second time period, and means for storing said responsive signal, where said responsive signal is said bioelectric or vital sign signal;

means for comparing said baseline signal and said responsive signal to determine any differences therebetween, said any differences relied upon to determine a state of the portion of the subject's body, said determined state excited by the first predetermined sound signal directed thereto during the second time period;

means for processing said determined state based on said baseline signal and said response signal from the portion of the subject's body to render a medical diagnosis; and means for recommending one or more courses of action and preventive intervention for the medical diagnosis;

wherein:
- the baseline and responsive signals are brain wave signals;
- the first predetermined sound is a low frequency, low amplitude sound;
- the differences determined between said baseline signal and said responsive signal is a differential in the brain wave activity; and
- the medical diagnosis is a thyroid problem.

18. The system of claim 17 wherein: the first predetermined sound:
- has a frequency of 125 Hz or less; and
- an amplitude increasing from 20 dB below ambient.

19. The system of claim 17 wherein:
the first predetermined sound signal is a low frequency sound whether emanating from a speaker or other vibrating structure or membrane and wherein said means for directing includes means for directing the predetermined low frequency sound starting at an amplitude defined as unperceivable by American society of heating, refrigerating and air-conditioning engineers ("ASHRAE") standards and increasing the amplitude until a perceptible amplitude is reached.

20. The system of claim 17 wherein:
said means for directing includes means for directing the first predetermined sound signal at a fixed frequency starting at an amplitude defined as unperceivable by American society of heating, refrigerating and air-conditioning engineers ("ASHRAE") and increasing the amplitude of the sound signal until an elevated amplitude is reached.

* * * * *